United States Patent
Gilad et al.

(12) 
(10) Patent No.: US 6,368,602 B1
(45) Date of Patent: Apr. 9, 2002

(54) MUCOSAL IMMUNIZATION AGAINST HEPATITIS A VIRUS (HAV) THROUGH RECTAL ADMINISTRATION OF HAV VACCINE

(75) Inventors: Mali Ketzinel Gilad, Jerusalem; Evelyn Zeira, Beit-Shemesh; Hilla Giladi, Mevaseret Zion; Eithan Galun, Har-Adar, all of (IL)

(73) Assignee: Hadasit Medical Research Services and Development Ltd, Jerusalem (IL)

( * ) Notice: Subject to any disclaimer, the term of this patent is extended or adjusted under 35 U.S.C. 154(b) by 0 days.

(21) Appl. No.: 09/596,060

(22) Filed: Jun. 16, 2000

(51) Int. Cl.$^7$ ................................................ A61K 39/29
(52) U.S. Cl. .................. 424/226.1; 424/184; 424/189.1; 424/204.1; 435/235.1; 435/236
(58) Field of Search ............................... 424/1.11, 1.53, 424/1.65, 1.69, 1.73, 9.1, 9.2, 9.3, 184.1, 189.1, 201.1, 204.1, 450, 226.1, 9.4, 9.5; 435/235.1, 236

(56) References Cited

U.S. PATENT DOCUMENTS

| | | | |
|---|---|---|---|
| 4,636,385 A | * | 1/1987 | Plotkin et al. ................. 424/89 |
| 6,017,513 A | * | 1/2000 | Betbeder et al. ............ 424/1.73 |
| 6,096,291 A | * | 8/2000 | Betbeder et al. ............ 424/1.69 |

OTHER PUBLICATIONS

Fields. *Fields Virology* (Philadelphia, PA, Lippincott Williams & Wilkins, 1995), pp. 665–666 and 699.*

Herremans et al, "Induction of Mucosal Immunity by Inactivate4d Poliovirus Vaccine is Dependant on Previous Mucosal Contact with Live Virus", *J. Immunol*, 15;162:5011–8, 1999.

Review: Vaccine supplement, *Nature Medicine*, 4:474–534, 1998.

Nardelli–Haefliger et al, "Oral and Rectal Immunization of Adult Female Volunteers With A Recombinant Attenuated Salmonella Typhi Vaccine Strain", *Infect Immun.*, 1996, 64:5219–24.

Lehner et al, "A Rational Basis for Mucosal Vaccination against HIV Infection", *Immunol. Rev*, 170:183–96, 1999.

Pagalieroni et al, "Cellular Immune Response to Hepatitis A Vaccine in Healthy Individuals with Delayed Seroconversion", 10$^{th}$ Int. Symposium on Viral Hepatitis at Atlanta, GA, Apr. 2000, Abstract 011.

* cited by examiner

Primary Examiner—Jeffrey Stucker
(74) Attorney, Agent, or Firm—D'Vorah Graeser

(57) ABSTRACT

A method for administering the HAV vaccine to a subject by absorption through a mucosal tissue, particularly through the mucosa of the rectum. The method of the present invention enables the HAV vaccine to be administered to the subject rectally, for example as a suppository or other rectal dosage form, and to successfully immunize the subject against HAV. Thus, the present invention overcomes problems of background art methods of administration, such as systemic administration by injection for example, which require needles, and which are difficult and expensive to perform.

6 Claims, 1 Drawing Sheet

Figure 1:
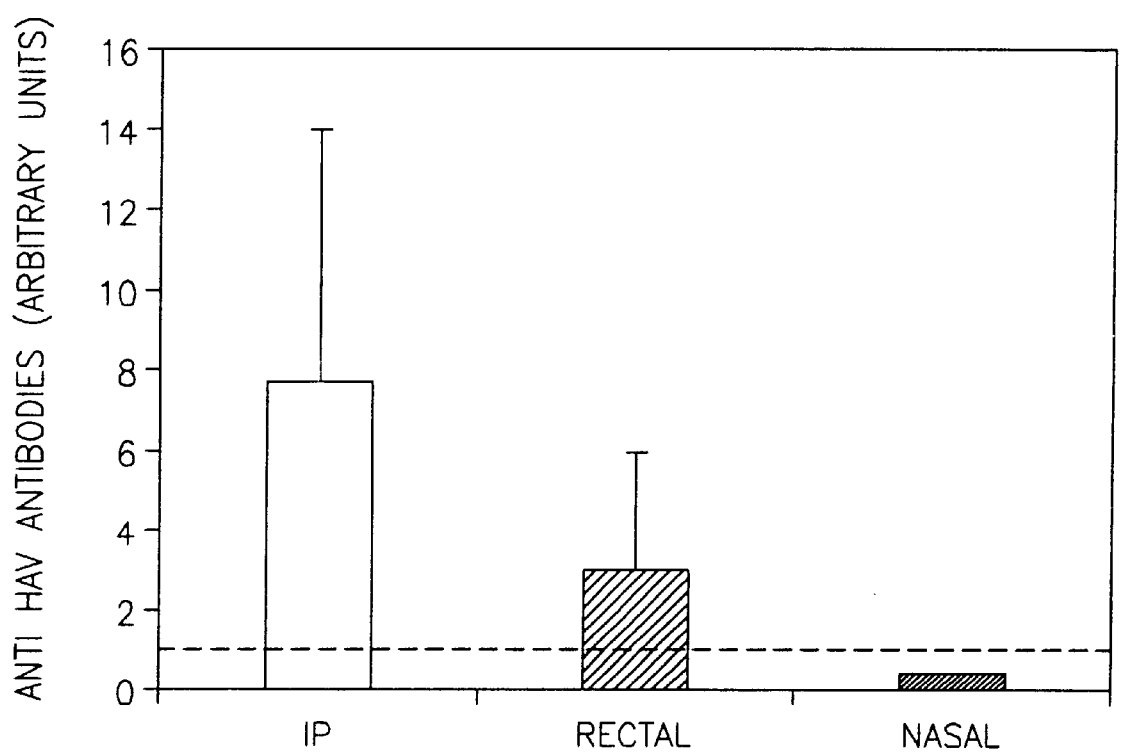

MUCOSAL IMMUNIZATION AGAINST HEPATITIS A VIRUS (HAV) THROUGH RECTAL ADMINISTRATION OF HAV VACCINE

FIELD AND BACKGROUND

The present invention relates to a method of immunizing a subject against Hepatitis A virus (HAV), and in particular, to such a method in which a vaccine against HAV is administered through the rectal mucosa of the subject.

Infectious diseases are a worldwide cause of morbidity and mortality. Such diseases particularly affect individuals with weaker immune systems, such as children, and are probably the primary worldwide killer of children (The World Health Report 1997, WHO). Travel and other contact between populations have caused the world to become an increasingly mixed environment in terms of the spread of micro-organisms, such as bacteria and viruses, thereby demanding a higher degree of protection for communities from such infectious agents.

The most efficient strategy, which has been proven to be effective in overcoming these major individual and community health problems, is prevention of the disease state by mass vaccination (Review: Vaccine supplement. Nature Medicine, 4:474–534,1998). However, in spite of the great recent progress in the understanding of the immune response and the development of biotechnological tools, the current technology for mass production of vaccines against a broad spectrum of indications is still very costly and in many cases practically unavailable. In addition, even if the vaccines are available, the administration of such vaccines currently requires a needle or other instrument for direct, systemic injection, with very few exceptions. Thus, mass vaccination programs currently require both a large supply of the vaccine, and of the requisite instruments for administering the vaccine, which can render such programs difficult or impossible to perform.

In particular, no mass vaccination program exists for Hepatitis A virus (HAV), a member of the genus Hepatovirus within the viral family *picornaviriade.* HAV vaccine is currently generated in tissue cultures, which produce a low viral titer, and is therefore expensive. The expense and difficulty of production are such that the HAV vaccine can currently only be purchased for small-scale programs. New modes for cheap and effective mass vaccination are needed. Providing a vaccine through a simple method could significantly increase the number of protected populations.

Recently, a number of investigators have suggested that vaccination against bacterial agents, such as salmonella, or viral agents, such as HIV, may possibly be enhanced through the rectal administration of attenuated or killed bacteria (see for example “Oral and rectal immunization of adult female volunteers with a recombinant attenuated Salmonella typhi vaccine strain”; Nardelli-Haefliger D, Kraehenbuhl J P, Curtiss R 3rd, Schodel F, Potts A, Kelly S, De Grandi P. Infect Immun. 1996;64:5219–24; and “A rational basis for mucosal vaccination against HIV infection”; Lehner T, Bergmeier L, Wang Y, Tao L, Mitchell E. Immunol Rev. 1999;170:183–96). Rectal, nasal or oral administrations of vaccines have elicited a humoral and in some cases cellular immune response, although such a response has been variable, indicating that vaccines against certain infectious agents may not be successfully administered through one or more of these routes of administration. For some of these vaccines, however, the humoral response generated neutralizing antibodies against the pathogen as proven in the case of the polio oral vaccine developed by Alfred Sabin.

Unfortunately, no such method for administering the HAV vaccine has been successful through a route of administration other than injection. Therefore, the HAV vaccine is currently difficult to administer, such that any mass vaccination program would be expensive and complicated to perform.

There is thus a need for, and it would be useful to have, a method for administering the HAV vaccine through a route other than direct systemic injection.

SUMMARY OF THE INVENTION

The present invention is of a method for administering the HAV vaccine to a subject by absorption through a mucosal tissue, particularly through the mucosa of the rectum. The method of the present invention enables the HAV vaccine to be administered to the subject rectally, for example as a suppository or other rectal dosage form, and to successfully immunize the subject against HAV. Thus, the present invention overcomes problems of background art methods of administration, such as systemic administration by injection for example, which require needles, and which are difficult and expensive to perform.

According to the present invention, there is provided a method for administering a viral vaccine to a subject, the viral vaccine being for a virus infecting the subject through a gastrointestinal mucosa, the method comprising the step of: (a) administering the viral vaccine to the gastrointestinal mucosa of the subject.

According to another embodiment of the present invention, there is provided a method for delivering at least one viral encapsidated gene through a gastrointestinal mucosa of a subject, the method comprising the step of: (a) administering the at least one viral encapsidated gene to the gastrointestinal mucosa of the subject.

BRIEF DESCRIPTION OF THE DRAWING

The foregoing and other objects, aspects and advantages will be better understood from the following detailed description of a preferred embodiment of the invention with reference to the drawing, wherein:

The FIGURE is a graph of the titer of experimental mice after administration of the HAV vaccine; six Balb/c mice were administered 20 μl nasally, 100 μl rectally or 100 μl into the peritoneum (IP) of a commercial preparation of the HAV vaccine (HAVRIX™). The HAVRIX™ vaccine contains a formaldehyde inactivated HAV, strain HM175, adsorbed to aluminum hydroxide. The vaccine was administered twice, at days 0 and 21, and tested for anti-HAV antibodies (HAVAB, EIA for total anti-HAV antibodies, Abbott) 35 days after the first vaccination.

DESCRIPTION OF THE PREFERRED EMBODIMENTS

The present invention is of a method for administering the HAV vaccine to a subject by absorption through a mucosal tissue, particularly through the mucosa of the rectum. The method of the present invention enables the HAV vaccine to be administered to the subject rectally, for example as a suppository or other rectal dosage form, and to successfully immunize the subject against HAV. Thus, the present invention overcomes problems of background art methods of administration, such as systemic administration by injection for example, which require needles, and which are difficult and expensive to perform.

The gastrointestinal tract is a major port of entry for a large group of viruses which impose a significant health burden. HAV, a plus strand RNA virus, is one such infectious agent. HAV enters the human body through the gastrointestinal system, and migrates to the liver for tissue specific replication, thereby causing liver damage and the concomitant development of clinical hepatitis.

In order to immunize the subject against the disease state caused by HAV, the present invention uses the rectal administration of a HAV vaccine, such as the currently available HAV vaccine, HAVRIX™ (SmithKline Beecham Biologicals), to a subject. As shown in the results below, the immune system of the subject is then able to recognize the viral nucleocapsid proteins following the presentation of viral peptides by the MHC type I molecules in M type cells or other APC's (antigen presenting cells) in the gut epithelium. Vaccines for polioviruses (another member of the picornavirus family) and other viral agents could be developed using the same principle, namely, employing the natural viral tropism to the epithelial cells covering the gastrointestinal tract.

The preferred vaccination strategy according to the present invention involves the exposure of the intestine to HAV related particles, thereby eliciting a humeral immune response and possibly a cellular response as recently shown ("Cellular immune response to hepatitis A vaccine in healthy individuals with delayed seroconversion"; $10^{th}$ International Symposium on Viral Hepatitis at Atlanta Ga. Apr. 9–13, 2000 by Pagalieroni T G et al. Abstract 011), with the resultant generation of anti-HAV neutralizing antibodies against HAV.

In order to test the method of the present invention, an animal model was developed for the assessment of anti-HAV antibody production in-vivo following rectal administration of HAVRIX™ (HAV vaccine) as a method of intestinal exposure to HAV related particles. The following experimental protocol was used. The HAV vaccine was administered to Balb/c mice via IP, intranasal and intrarectal routes, at days 0 and 21. Six balb/c mice were administered 20 microliters nasally, 100 microliters rectally or 100 microliters into the peritoneum (IP) of a commercial preparation of the HAV vaccine (HAVRIX™), at a concentration of 720 EL.U./ml for the antigen. EL.U. stands for Enzyme-linked immunosorbent assay (ELISA) units.

The mice were then tested for anti-HAV antibodies (HAVAB, EIA for total anti-HAV antibodies, Abbott Laboratories, Diagnostic Division, Abbott Park Ill., USA) 35 days after the first vaccination.

As seen in the FIGURE, mice which received the vaccine through the IP (positive control) or intrarectal routes, developed anti-HAV antibodies, whereas mice which received the intranasal vaccine did not show any humeral immune response. This suggests that following the rectal administration, the viral capsid proteins were presented to the immune system of the mice. This presentation resulted in the generation of anti-HAV antibodies from the IgG class and probably from the IgA class also. As previously shown for the polio vaccine, administration through the oral mucosa elicited the generation of antibodies of both the IgG and IgA classes (see for example "Induction of mucosal immunity by inactivated poliovirus vaccine is dependent on previous mucosal contact with live virus"; Herremans T M, Reimerink J H, Buisman A M, Kimman T G, Koopmans M P. J Immunol. 1999 15;162:5011–8).

In cases in which viruses enter the human body from the gut epithelium the role of the IgA type of antibodies is essential to neutralize the virus at the portal of entry, as IgA is the type of antibody which is secreted to the gut lumen.

However, after the intramuscular (IM) administration of vaccines, only IgG class antibodies are generated, as shown in the polio vaccine upon IM injection. Similarly, HAV vaccines, which have only been administered through IM injection until now, have only been shown to produce IgG class antibodies. As for successful immunization against polio, clearly the IgA class of antibodies must be generated to neutralize viruses near the gut epithelium to prevent infection by HAV. The method of the present invention, in which the HAV vaccine is administered to the body through the rectal mucosa, could have a major advantage over the current vaccination program, by blocking the viral portal of entry. In addition, the method of the present invention is able to induce the generation of a successful immune response against HAV, without requiring needles or other invasive instruments for administration.

Thus, these results clearly show that the intrarectal route is a suitable method for the generation of protective vaccination against HAV, and also other viruses that enter the body through the gastrointestinal system.

The present invention thus enables the rectal administration of an HAV vaccine such as HAVRIX™ (HAV vaccine) for the generation of an anti-HAV immune response, thereby eliciting neutralizing antibodies against HAV.

Without wishing to limit the present invention, a suitable dosage of the HAV vaccine is preferably in the range of from about 0.75 to about 7500 EL.U. of the antigen for each administration, more preferably approximately 75 EL.U. of the antigen, applied to the rectum in a suppository, cream, liquid, tablet, or any other solid, semi-solid or liquid dosage form which is suitable for the administration of HAV antigen to the rectal mucosa.

The method of the present invention is also optionally and preferably suitable for the administration of at least one viral encapsidated gene through the gastrointestinal mucosa of the subject, and particularly through the rectal mucosa. In this optional but preferred method, the viral encapsidated gene or genes is administered to the gastrointestinal mucosa of the subject, in a substantially similar manner as for the previously described HAV vaccine. Thus, the present invention also provides a method for administering one or more viral encapsidated gene or genes to the subject through the gastrointestinal, and particularly the rectal, mucosa.

While the invention has been described with respect to a limited number of embodiments, it will be appreciated that many variations, modifications and other applications of the invention may be made.

What is claimed is:

1. A method for delivering at least one viral encapsidated gene through a gastrointestinal mucosa of a subject, the method comprising the step of:

(a) administering the at least one viral encapsidated gene to the gastrointestinal mucosa of the subject, wherein the at least one viral encapsidated gene is from HAV (Hepatitis A virus) and wherein the at least one viral gene is encapsidated in HAV.

2. The method of claim 1, wherein the at least one viral encapsidated gene is for a virus infecting the subject through the gastrointestinal mucosa.

3. The method of claim 2, wherein the gastrointestinal mucosa is a rectal mucosa, such that step (a) is performed by administering the viral vaccine to the rectal mucosa of the subject.

4. The method of claim 3, wherein the viral vaccine is in a form of a suppository.

5. The method of claim 1, wherein the subject is a lower mammal.

6. The method of claim 1, wherein the subject is a human.

* * * * *